(12) United States Patent
Diamond et al.

(10) Patent No.: US 9,201,006 B2
(45) Date of Patent: *Dec. 1, 2015

(54) IMAGING APPARATUS AND METHOD

(71) Applicant: Geoffrey Graham Diamond, Warwickshire (GB)

(72) Inventors: Geoffrey Graham Diamond, Warwickshire (GB); Tat Hean Gan, Taiping Perak (MY); David Arthur Hutchins, Coventry (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/677,474

(22) Filed: Apr. 2, 2015

(65) Prior Publication Data

US 2015/0226668 A1    Aug. 13, 2015

Related U.S. Application Data

(63) Continuation of application No. 12/306,505, filed as application No. PCT/GB2007/050368 on Jun. 28, 2007.

(30) Foreign Application Priority Data

Jun. 28, 2006 (GB) .................................. 0613165.0

(51) Int. Cl.
*G01N 21/59* (2006.01)
*A61B 5/00* (2006.01)
*G01N 21/47* (2006.01)
*G01N 21/55* (2014.01)
*G01N 21/359* (2014.01)

(52) U.S. Cl.
CPC .............. *G01N 21/59* (2013.01); *A61B 5/0059* (2013.01); *G01N 21/4795* (2013.01); *G01N 21/55* (2013.01); *A61B 5/4547* (2013.01); *G01N 21/359* (2013.01); *G01N 2021/558* (2013.01)

(58) Field of Classification Search
CPC ... G01N 21/59; G01N 21/4795; G01N 21/55; G01N 21/35; G01N 21/359; G01N 2021/558; G01N 2021/3155; G01N 21/31; A61B 5/0059; A61B 5/4547; A61B 5/441; G05D 1/0242; H04N 5/33; H04N 3/09; H04N 5/332
See application file for complete search history.

(56) References Cited

U.S. PATENT DOCUMENTS

| 3,961,194 | A | * | 6/1976 | Simon et al. ................... 250/334 |
| 4,009,392 | A | * | 2/1977 | Hanley ........................ 250/338.1 |
| 4,283,629 | A | * | 8/1981 | Habermehl et al. .............. 378/4 |
| 4,317,998 | A | * | 3/1982 | Dore ............................. 250/347 |
| 4,321,594 | A | * | 3/1982 | Galvin et al. .................. 340/567 |
| 4,414,833 | A | * | 11/1983 | Nicolas et al. ................. 72/19.1 |

(Continued)

*Primary Examiner* — Manav Seth
(74) *Attorney, Agent, or Firm* — Daniel S. Polley, P.A.

(57) ABSTRACT

Apparatus for inspecting an article comprising: a controller configured to generate a drive signal having a periodic amplitude variation; a source, the source being operable by the controller to emit a source beam thereby to irradiate an article, the source beam comprising a beam of electromagnetic radiation having a periodic amplitude variation corresponding to that of the drive signal; and a detector, the detector being configured to detect a portion of the source beam that has been transmitted through at least a portion of the article, and to generate a detector signal having an amplitude variation corresponding to the amplitude variation of said portion of the source beam, the controller being further configured to generate a difference value corresponding to a difference between the amplitude of the detector signal and the amplitude of a reference signal.

29 Claims, 14 Drawing Sheets

(56) References Cited

U.S. PATENT DOCUMENTS

| | | | | |
|---|---|---|---|---|
| 4,515,165 A | * | 5/1985 | Carroll | 600/475 |
| 4,907,441 A | * | 3/1990 | Shurmer | 73/23.2 |
| 4,914,672 A | * | 4/1990 | Hebrank | 374/124 |
| 4,933,669 A | * | 6/1990 | Lyons | 340/632 |
| 5,101,880 A | * | 4/1992 | Fujiwara et al. | 164/154.4 |
| 5,372,936 A | * | 12/1994 | Fraatz et al. | 435/34 |
| 5,436,457 A | * | 7/1995 | Tomita | 250/343 |
| 5,477,051 A | * | 12/1995 | Tsuchiya | G01N 21/4795 250/339.12 |
| 5,571,401 A | * | 11/1996 | Lewis et al. | 205/787 |
| 5,585,575 A | * | 12/1996 | Corrigan et al. | 73/863.71 |
| 5,673,746 A | * | 10/1997 | Chun et al. | 164/454 |
| 5,675,070 A | * | 10/1997 | Gelperin | 73/23.34 |
| 5,801,297 A | * | 9/1998 | Mifsud et al. | 73/23.34 |
| 6,075,882 A | * | 6/2000 | Mullins et al. | 382/141 |
| 6,085,576 A | * | 7/2000 | Sunshine et al. | 73/29.01 |
| 6,519,744 B2 | * | 2/2003 | Seidel et al. | 438/7 |
| 6,522,407 B2 | * | 2/2003 | Everett et al. | 356/369 |
| 6,927,857 B2 | * | 8/2005 | Koele et al. | 356/431 |
| 6,996,478 B2 | * | 2/2006 | Sunshine et al. | 702/22 |
| 7,312,454 B2 | * | 12/2007 | Safai et al. | 250/347 |
| 7,627,365 B2 | * | 12/2009 | Chance | 600/475 |
| 7,746,236 B2 | * | 6/2010 | Cole | 340/577 |
| 7,756,305 B2 | * | 7/2010 | Price | 382/128 |
| 7,850,077 B2 | * | 12/2010 | Talwerdi et al. | 235/382 |
| 8,363,887 B2 | * | 1/2013 | Haas et al. | 382/100 |
| 8,933,405 B2 | * | 1/2015 | Diamond | 250/339.07 |
| 2011/0228087 A1 | * | 9/2011 | Hsieh | 348/143 |

* cited by examiner

FIG. 8A  FIG. 8B  FIG. 8C
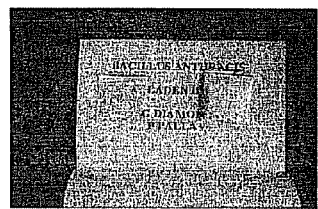 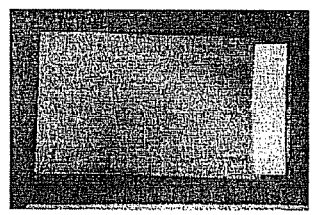 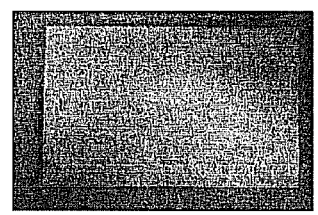
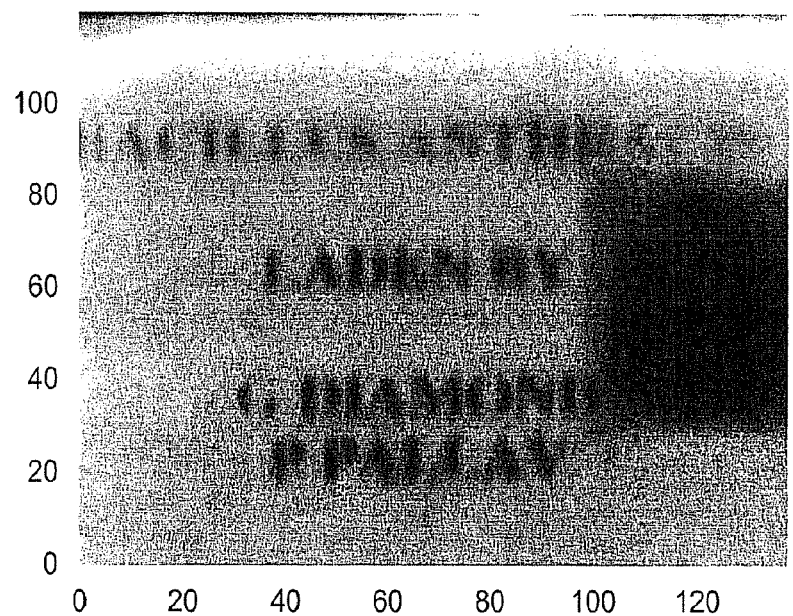
FIG. 8D

FIG. 9A
FIG. 9B
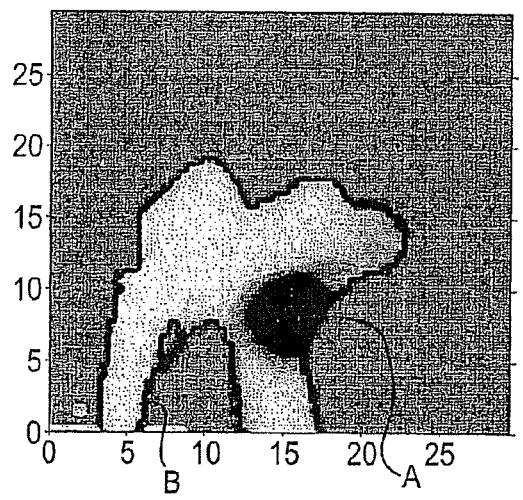
FIG. 9C
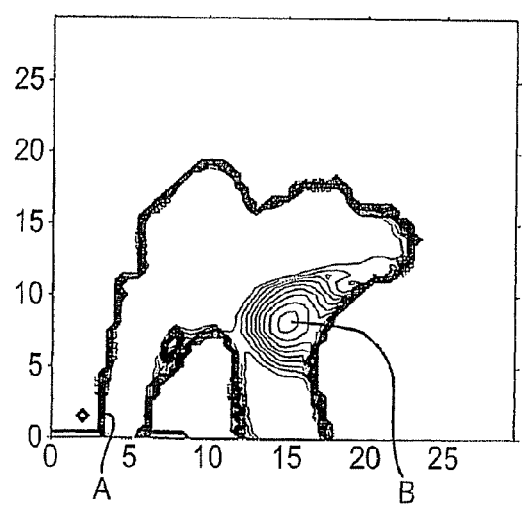
FIG. 9

FIG. 10A
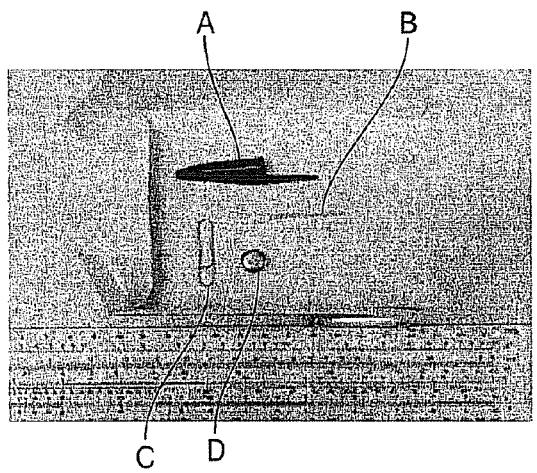
FIG. 10B
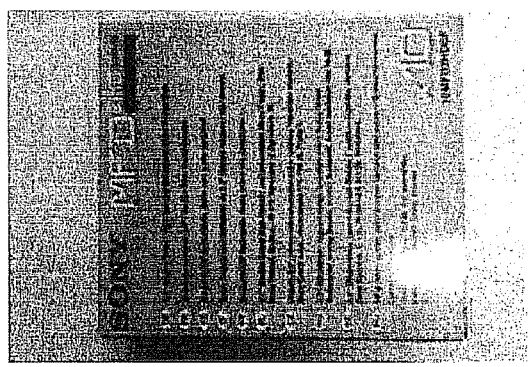
FIG. 10C
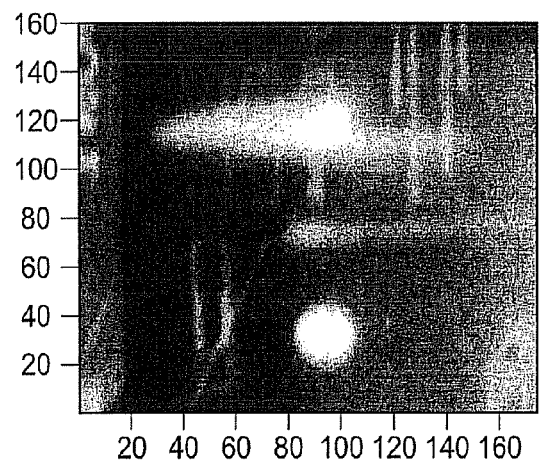
FIG. 10D
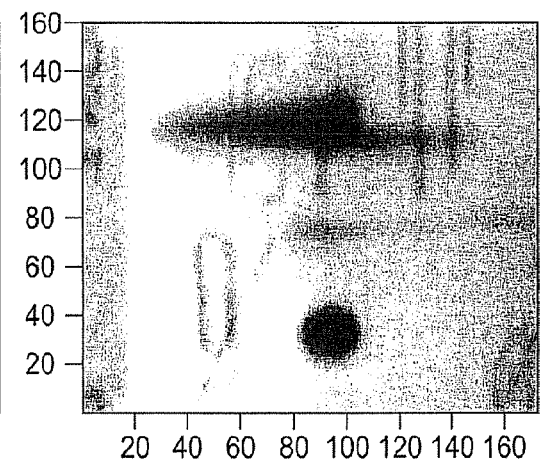
FIG. 10

IMAGING APPARATUS AND METHOD

This application is a continuation of U.S. Application Ser. No. 12/306,505, file Dec. 23, 2008, which application is a 35 U.S.C. 371 filing of PCT/GB07/50368, filed Jun. 28, 2007, which application claims priority to and the benefit of United Kingdom Application No. 0613165.0, filed Jun. 28, 2006.

FIELD OF THE DISCLOSURE

The present disclosure relates to imaging apparatus and to a method for investigating an internal structure of an article. In particular, but not exclusively, the disclosure relates to apparatus and method for imaging concealed objects.

BACKGROUND

Existing technologies such as x-ray imaging systems have been used to investigate the internal structure and properties of a range of objects including food products and the human body. However, systems employing X-rays (or other ionizing radiation) suffer from a range of health and safety concerns. Ionizing radiation is known to be capable of causing damage to tissue and other materials. Consequently, equipment employing x-ray radiation must be provided with sufficient screening to ensure operating and other personnel are not exposed to the radiation.

In addition, the size of an x-ray system is large, and consequently not appropriate in certain manufacturing situations. A further drawback of X-ray systems is the relatively high cost of an X-ray imaging system.

Terahertz imaging systems have also been employed for imaging an internal structure of an article. However, imaging water-containing samples using these systems is challenging due to the high attenuation of terahertz frequency signals by water molecules.

SUMMARY

There is provided an apparatus for inspecting an article comprising:
a controller configured to generate a drive signal having a periodic amplitude variation;
a source, the source being operable by the controller to emit a source beam thereby to irradiate an article, the source beam comprising a beam of electromagnetic radiation having a periodic amplitude variation corresponding to that of the drive signal; and
a detector, the detector being configured to detect a portion of the source beam that has been transmitted through at least a portion of the article, and to generate a detector signal having an amplitude variation corresponding to the amplitude variation of said portion of the source beam.

The controller can be further configured to generate a difference value corresponding to a difference between the amplitude of the detector signal and the amplitude of a reference signal.

The apparatus according to at least some of the embodiments of the disclosure is capable of providing an image of an internal structure of an article without exposing the article to ionizing radiation. Furthermore, the apparatus according to at least some of the embodiments of the disclosure does not require ionizing radiation shields or other precautions associated with prior art techniques such as X-ray imaging.

Furthermore, the apparatus according to at least some of the embodiments of the disclosure can be less costly than X-ray imaging systems. At least some of the embodiments of the disclosure require less power than X-ray imaging systems and are substantially more portable.

Preferably, the reference signal is a periodic signal and can have the same frequency as the drive signal. Preferably the amplitude of the reference signal can correspond to the amplitude of the drive signal.

The apparatus may be configured to implement a homodyning function between the reference signal and the detector signal thereby to generate the difference value.

Preferably the reference signal can correspond substantially to the drive signal.

In at least some of the embodiments of the disclosure, the detector signal can be combined with a reference signal corresponding to the drive signal thereby to generate a signal corresponding to the difference in amplitude between the drive signal and the detector signal.

Preferably the apparatus can be configured to implement an autocorrelation function between the reference signal and the detector signal thereby to generate the difference value.

Preferably the apparatus can be configured to implement a lock-in detection function between the reference signal and the received signal thereby to generate the difference value.

Use of a reference signal having the same frequency as the drive signal has the advantage that any variations in the frequency of the drive signal are exactly mirrored in the variation of the reference signal. Thus, the difference value may be made substantially independent of variations in the drive signal frequency. Variations in the drive signal frequency may arise for example due to variations in temperature of the electronics associated with the apparatus.

Alternatively or in addition, the reference signal may be a periodic reference signal having a frequency different from the drive signal.

The apparatus may be configured to implement a heterodyning function between the reference signal and the detector signal thereby to generate the difference value.

Thus, in at least some of the embodiments of the disclosure, the detector signal can be combined with a reference signal having a different frequency to the drive signal. In at least some embodiments of the disclosure the combined signal is passed through a low pass filter arranged to pass a signal of a beat frequency corresponding to the difference between the frequency of the reference signal and the frequency of the detector signal.

Preferably the beam of electromagnetic radiation corresponds to electromagnetic radiation having a wavelength in the range 700 to 2000 nm. This range will also be referred to hereinafter as 'near infrared' or 'NIR' radiation.

This range of wavelength can correspond to a range in which many materials are relatively transparent to electromagnetic radiation. In other words, this range of wavelength can correspond to a range in which a sufficient amount of radiation may be transmitted through a sample to enable inspection of an internal structure of the sample to be made in a reasonable length of time.

This range of wavelength can also correspond to wavelengths to which water is relatively transparent to electromagnetic radiation. Thus, imaging of the internal structure of water-containing materials such as biological materials is possible. Thus, apparatus according to at least some of the embodiments have the advantage over prior art techniques such as terahertz (THz) imaging techniques that water-containing materials can be imaged. Electromagnetic signals in the THz range of frequencies are strongly absorbed by water, rendering the imaging of the internal structure of biological materials difficult. Whilst THz systems have demonstrated an ability to provide contrast between dry materials, such as between paper without an ink thereon and paper with an ink thereon, they have not been able to demonstrate an ability to provide contrast in biological materials.

Conversely, X-ray imaging systems have demonstrated an ability to provide contrast in biological materials, but have not been able to provide contrast in samples with relatively small concentrations of a different material. For example, X-ray imaging systems are unable to distinguish between paper with an ink thereon and paper without an ink thereon.

The range of frequencies from 700 to about 2000 nm has the advantage that heating of a sample as the electromagnetic radiation passes through the sample does not occur to a significant extent.

At least some of the disclosed embodiments can be able to distinguish (i.e. provide contrast enabling discrimination between) cysts and tumours in biological materials.

In the case of a cyst, being essentially a water-filled sack, the cyst does not scatter the electromagnetic signal, but rather attenuates the signal. In the case of a tumour or cancer, having a cellular structure on a scale of the order of 1 .mu.m, scattering of the electromagnetic signal occurs. This difference in interaction between the sample and the incident radiation enables more accurate determination of the nature of a feature (such as a cyst or a tumour) in a biological sample to be made. Thus, the apparatus according to at least some embodiments may be used in the detection and characterisation of cysts, tumours and other biological features of a body. Being able to distinguish between cysts and tumours enables medical practitioners to determine the nature and relative urgency of a medical procedure in respect of a given patient.

At least some of the embodiments of the disclosure can provide utility in clinical screening and investigation of patients.

The beam of electromagnetic radiation may correspond to electromagnetic radiation having a wavelength in the range 700 to 1000 nm. In some embodiments the beam of electromagnetic radiation corresponds to electromagnetic radiation having a wavelength in the range 800 to 900 nm.

Preferably the periodic amplitude variation can correspond to a square wave signal.

Alternatively or in addition, the periodic amplitude variation may correspond to a sine wave signal.

The apparatus may be operable to move the detector with respect to the article to be inspected.

Alternatively or in addition, the apparatus may be operable to move the article to be inspected with respect to the detector. Thus, inspection of a plurality of areas of a sample may be performed without the need to provide a corresponding plurality of detectors. Thus, the detector may be moved to an area of the sample where it is desirable to inspect the sample, and a measurement made of a signal transmitted by the source.

In some embodiments of the disclosure, the relative position of the source with respect to the detector remains substantially unchanged whether the detector is moved with respect to the sample or the sample is moved with respect to the detector.

Preferably the detector can comprise a photodetector element.

More preferably, the detector can comprise an array of photodetector elements. Thus, parallel collection of data may be performed. In other words, detection of electromagnetic radiation from the source that has interacted with the article to be inspected may be made at a plurality of spatially separate locations at substantially the same time. Thus, data can be collected from a plurality of spatially separate locations more quickly that in the case of serial collection of data. By serial collection of data is meant that data is collected from one spatial location, and subsequently from a second spatial location.

The array may be a linear array. Alternatively the array may be a planar array. With a planar array data may be obtained over a two dimensional area without a requirement to move the detector or the article under inspection.

The apparatus may be configured to operate in a transmission mode whereby the detector is arranged to detect a beam of electromagnetic radiation transmitted through the article to be inspected from one side of the article to the other, the detector being provided on a side of the sample substantially opposite a side wherein the source is provided.

Alternatively or in addition, the apparatus may be configured to operate in a reflection mode whereby the detector is arranged to detect a beam of electromagnetic radiation reflected by the article to be inspected, the detector being provided on substantially the same side of the article as the source.

By reflected is included reflection from an outer surface of the article as well as reflection from an inner volume of the article such as an interface between a matrix and an embedded particle. It will be understood by those skilled in the art that the reflection mode of operation therefore includes detection of electromagnetic radiation that has been transmitted through at least a portion of the article under inspection, and is not limited only to detection of electromagnetic radiation reflected from an outer surface of the article.

In a variation of the reflection mode of operation, in some embodiments of the disclosure one or more reflective elements are provided to reflect electromagnetic radiation transmitted through the specimen back through the specimen to a detector provided on substantially the same side of the specimen as the source.

The apparatus may be configurable to operate in either a reflection mode or a transmission mode.

The apparatus may be configurable to operate in a reflection mode and a transmission mode simultaneously.

The source may be configured to emit electromagnetic radiation of a plurality of wavelengths.

The detector may be configured to detect electromagnetic radiation of a plurality of wavelengths.

A plurality of detectors may be provided, each detector being configured to detect electromagnetic radiation of a different respective wavelength or range of wavelengths. Thus, the apparatus may be used to measure an amount of radiation absorbed by a sample as a function of wavelength of the radiation substantially simultaneously.

The detector may comprise a tunable filter. Thus, the same detector may be used to measure the amount of radiation incident upon the detector of each of a plurality of wavelengths or range of wavelengths. That is, by performing a plurality of measurements of an amount of electromagnetic radiation detected by the detector, and changing the characteristics of the filter between measurements, the relative amounts of attenuation of a signal by the sample as a function of wavelength may be determined.

At least one of said wavelengths may correspond to a characteristic absorption wavelength of a sample. Thus, analysis of a chemical or other composition of a material may be performed. That is, the apparatus may be used to assist in a determination as to whether a particular material, element or compound is present in an article under inspection.

The source may be a laser source. With laser sources, collimation of a beam of radiation from the source is not required. In at least some of the embodiments of the disclosure a laser beam in the form of a line is provided, the line being scanned across the sample thereby to obtain an image of a cross-sectional area of the sample, in a similar manner to laser barcode scanning technology.

In some embodiments of the disclosure a single source such as an LED or solid state laser is employed, in combination with a cylindrical lens in order to generate a linear beam with a relatively flat intensity distribution. In other words, the intensity distribution is substantially non-Gaussian.

At least one of the source and the detector may comprise a fiber optic cable.

The source may be provided with a fiber optic cable, the cable being arranged to direct the beam of electromagnetic radiation onto the article to be inspected.

Alternatively or in addition, the detector may be provided with a fiber optic cable arranged to direct electromagnetic radiation from the sample onto the detector.

There is also provided a method of inspecting an article comprising the steps of:

generating a drive signal having a periodic amplitude variation;

generating a source beam of electromagnetic radiation having a periodic amplitude variation corresponding to that of the drive signal;

passing a portion of the source beam through at least a portion of an article to be inspected and to a detector;

generating a detector signal having an amplitude variation corresponding to the amplitude variation of the portion of the source beam passed to the detector; and generating a difference value corresponding to a difference between the amplitude of the detector signal and the amplitude of a reference signal.

Preferably the source beam can correspond to electromagnetic radiation having a wavelength in the range of 700 to 2000 nm.

More preferably, the source beam can correspond to electromagnetic radiation having a wavelength in the range of 700 to 1000 nm.

Embodiments of the disclosure will now be described with reference to the accompanying figures in which:

BRIEF DESCRIPTION OF THE DRAWINGS

FIG. 8A, FIG. 8B, FIG. 8C and FIG. 8D show a series of images corresponding to a first example;

FIG. 10 consists of FIG. 10A, FIG. 10B, FIG. 10C and FIG. 10D which show a series of images corresponding to a third example;

DETAILED DESCRIPTION

Figure 1:
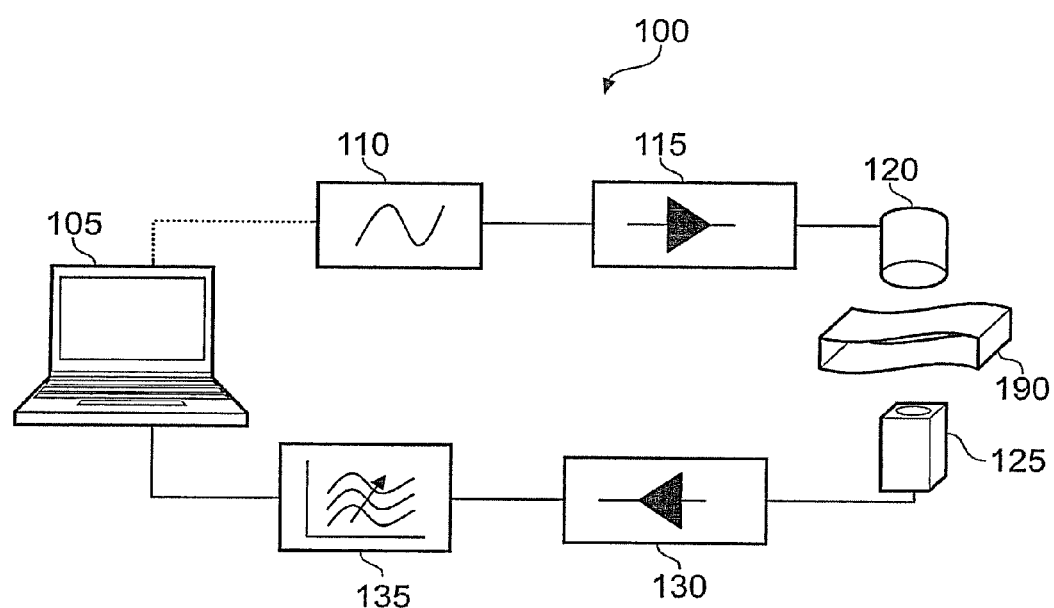
FIG. 1 shows a schematic illustration of apparatus according to a first embodiment of the disclosure.

According to a first embodiment, apparatus 100 for inspecting a sample can be substantially as shown schematically in FIG. 1. The apparatus is configured to operate in a homodyne mode. In other words, the drive signal and the reference signal are provide by the same signal generator.

Apparatus 100 can comprises a computing device 105, a reference (drive) signal generator 110, a reference (drive) signal amplifier 115, a radiation source 120, a radiation detector 125, a detector signal amplifier and conditioner 130 and a signal processing module 135.

Reference signal generator 110 can be configured to generate a periodic square wave having a frequency of 10 MHz. It will be appreciated that other frequencies are also useful. In some embodiments the square wave has a periodic frequency of between 1 MHz and 500 MHz.

In at least some embodiments of the disclosure computing device 105 can be configured to generate the reference signal instead of a separate reference signal generator 110.

Radiation source 120 according to the first embodiment can be a solid state light emitting diode (LED) device configured to emit electromagnetic radiation with a wavelength of around 900 nm. Other wavelengths are also useful and considered within the scope of the disclosure.

Radiation detector 125 can be a solid state detector having a two dimensional array of detector elements. According to the first embodiment the detector elements can be solid state diodes.

Other detector elements are also useful and considered within the scope of the disclosure. In some embodiments the detectors can be CMOS detectors. In other embodiments of the disclosure CCD detectors can be used. In at least some embodiments, any suitable commercially available infra-red camera can be used.

In the case that two dimensional arrays of detector elements are used, a lens may be provided to project an image of the sample onto the detector elements.

Detector 125 has an optical bandpass filter arranged to allow only radiation having a wavelength of substantially 900 nm to be incident upon the array of diodes. Bandpass filters corresponding to other wavelengths are also useful.

Variable optical bandpass filters arranged to transmit wavelengths of a different value or range of values can also be used. A diffraction grating can also be used. An adjustable diffraction grating can also be used.

Detector 125 can also be configured to generate a detector signal corresponding to the amplitude variation of the electromagnetic radiation detected by each of the elements of the detector 125.

The amplifier and conditioner 130 is arranged to process the signal generated by the detector 125 before it is passed to the signal processing module 135.

The amplifier and conditioner 130 performs a precursor function to the signal processing module 135 and is configured to remove extraneous noise.

The amplifier and conditioner 130 can be an electrical bandpass filter tuned to the reference signal generated by the reference signal generator 110. The amplifier and conditioner 130 can have two main functions. Firstly, it performs a relatively coarse filtering of the detector signal prior to the main signal recovery process (autocorrelation) performed by the signal processing module 135. Secondly, the amplifier and conditioner 130 removes harmonics that would otherwise interfere with the autocorrelation performed by the signal processing module.

Signal processing module 135 can be provided with a feed of the signal generated by the reference signal generator 110 and a feed of the detector signal following processing by the amplifier and conditioner 130. The signal processing module 135 is configured to perform an autocorrelation of the two signals and to produce an output corresponding to a difference in amplitude of the two signals for each of the elements of the detector 125. In other words, the signal processing module 135 is configured to provide an output that varies in a manner corresponding to variations in the amplitude of the electromagnetic signal passed through a portion of the sample from the source.

Autocorrelation and other lock-in detection techniques have the advantage of enabling substantially noise free data to be obtained. That is, the apparatus is able to filter out of the detector signal frequencies that do not correspond to the reference signal. This enables a more precise comparison of the relative amplitudes of the reference signal and detector signal to be made.

Since the difference in amplitude between the reference signal and the detector signal is small, small signal recovery techniques such as autocorrelation and other lock-in detection techniques provide a valuable means for determining the difference in amplitude between the signals, and thereby recording of a variation in the amplitude of the electromagnetic signal passed through a portion of the sample.

The reference signal and the detector signal can be signals of the same frequency, and therefore other homodyning techniques are also useful in determining a diffirence in amplitude of the two signals and considered within the scope of the disclosure.

In some embodiments, heterodyning techniques are used. In some embodiments, a reference signal of a different frequency to the source signal can be used.

In some embodiments, the reference signal is mixed with the detector signal to generate a beat signal. Variations in the amplitude of the beat signal may then be used to measure variations in the amplitude of the detector signal.

In some embodiments, a reference signal corresponding to harmonic frequencies of the drive signal is used. This enables harmonic analysis to be performed. This enables further information about an article under inspection to be determined.

In some embodiments employing homodyne techniques the reference (drive) signal is configured to provide a swept frequency signal. That is, the periodic frequency of the reference signal (whether the reference signal corresponds to a square wave signal, a sine wave signal or any other suitable signal) is varied as a function of time. In some embodiments a reference signal can be chirped. Other techniques may also be employed to improve the quality of the comparison of the relative amplitudes of the reference and detector signals and are considered within the scope of the disclosure.

According to the first embodiment, autocorrelation is performed using single frequency lock-in by means of an analogue circuit. Analogue circuits may be constructed having very high sensitivity to small differences in the amplitudes of the reference and detector signals, enabling high quality images of an internal structure of an article to be obtained.

In some embodiments, autocorrelation is performed digitally. Digital performance of autocorrelation allows it to be performed using a computer running a software program. However, analog to digital (A/D) conversion of the detector signal is needed before autocorrelation may be performed. The process of quantization of the detector signal in conversion from an analog to a digital signal inherently results in a loss of information and therefore a reduction in the quality of data resulting from the autocorrelation process.

In at least some other embodiments, the apparatus is configured to employ other types of small signal recovery techniques including a variety of other lock-in detection techniques. For example, standard multi channel analysers could be employed, or free-running, highly tuned filters that are unconnected and independent of the source. Heterodyning techniques could also be employed as discussed above, or software based signal threshold triggering and averaging techniques used.

Figure 2:
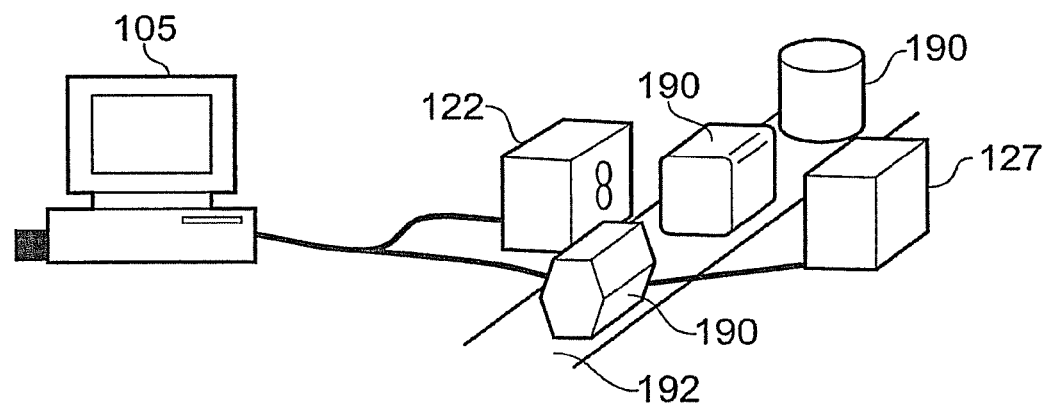
FIG. 2 shows a schematic illustration of apparatus according to the first embodiment of the disclosure.

FIG. 2 is a schematic diagram of the first embodiment arranged to analyze articles 190 passing through the apparatus on a conveyor belt 192.

According to the first embodiment the reference signal generator 110, reference signal amplifier 115 and radiation source 120 are provided in a single housing 122. Similarly, the radiation detector 125, radiation detector signal amplifier and conditioner 130 and signal processing module 135 are also provided in a single housing 127.

The apparatus shown in FIG. 1 can be arranged to operate in a transmission mode. In other words, the apparatus is configured such that the detector is arranged to detect a beam of electromagnetic radiation transmitted through the article to be inspected. Consequently, the detector 125 is provided on an opposite side of the article to be inspected with respect to the source 120.

In at least some other embodiments, a different arrangement of the relative locations of the source 120 and the detector 125 may be envisaged.

Figure 3:
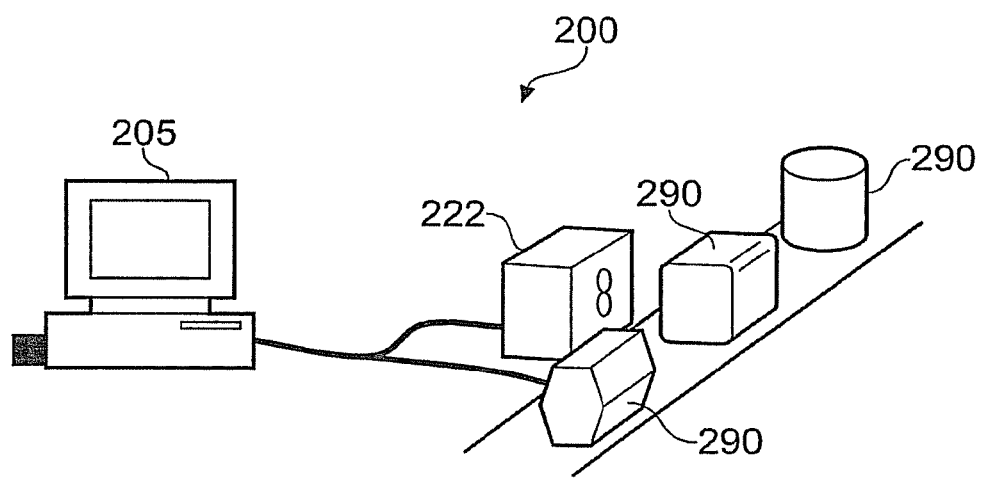
FIG. 3 shows a schematic illustration of apparatus according to a second embodiment of the disclosure.

In apparatus 200 according to a second embodiment, the apparatus can bearranged to operate in a reflection mode (FIG. 3). In other words, the apparatus is configured such that the detector is arranged to detect a beam of electromagnetic radiation reflected from the article to be inspected.

Thus, the reference signal generator, reference signal amplifier, radiation source, radiation detector, radiation detector signal amplifier and conditioner, and the signal processing module may be provided in a single housing 222. The source and detector are arranged to be located on the same side of the article 290 that is to be inspected with respect to each other.

In some embodiments, detectors are provided at locations on both sides of a sample to be inspected, allowing either or both of a transmission mode or a reflection mode of operation to be performed.

Figure 4:
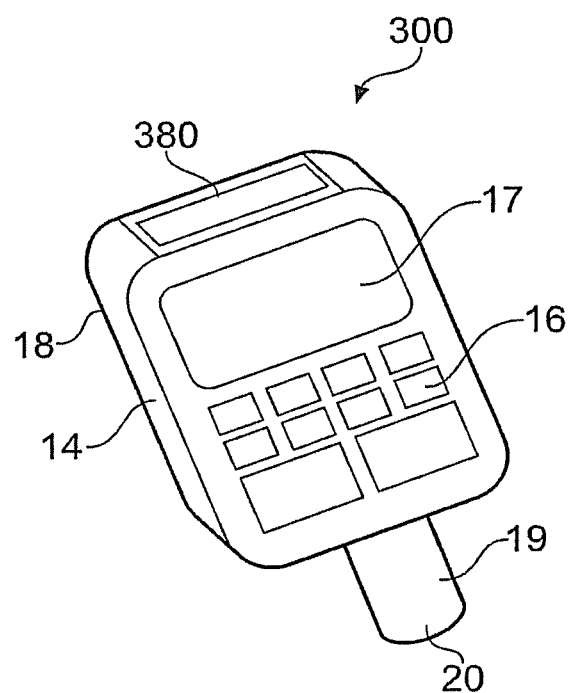
FIG. 4 shows a schematic illustration of apparatus according to a third embodiment of the disclosure.

Apparatus 300 according to the third embodiment (FIG. 4) can be in the form of a handheld device. The apparatus 300 is arranged to allow a sample to be inserted into a sample chamber 380. Inspection of a sample in the chamber 380 is performed in substantially the same manner as in the case of the first embodiment. In some embodiments in the form of a handheld device the device is configured to operate in a reflection mode.

Figures 5A, 5B:
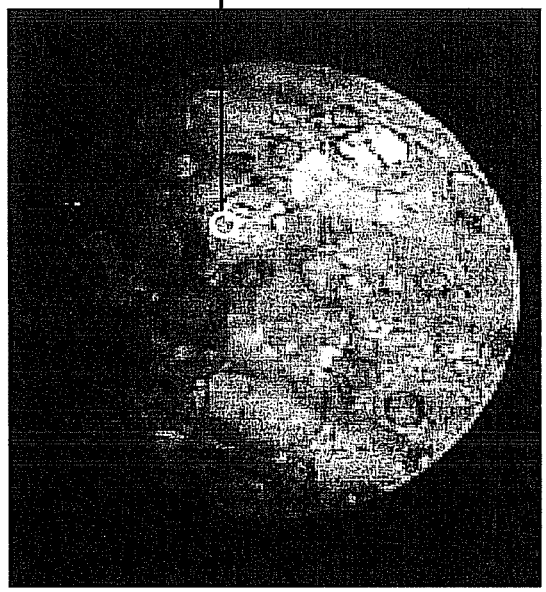
FIG. 5A shows an image obtained from a sample using apparatus according to an embodiment of the disclosure.
FIG. 5B shows pixel values corresponding to an area of the image.

FIG. 5 (a) shows an image of a portion of a food sample obtained by means of apparatus according to the first embodiment. FIG. 5(b) is a schematic illustration of a portion of an array of pixels of the image corresponding to the area circled in FIG. 5(a). Each pixel corresponds to a detector element of the detector 125. Overlaid on each pixel is a number corresponding to the amplitude of the signal generated by the detector element corresponding to that pixel.

Figures 6A, 6B:
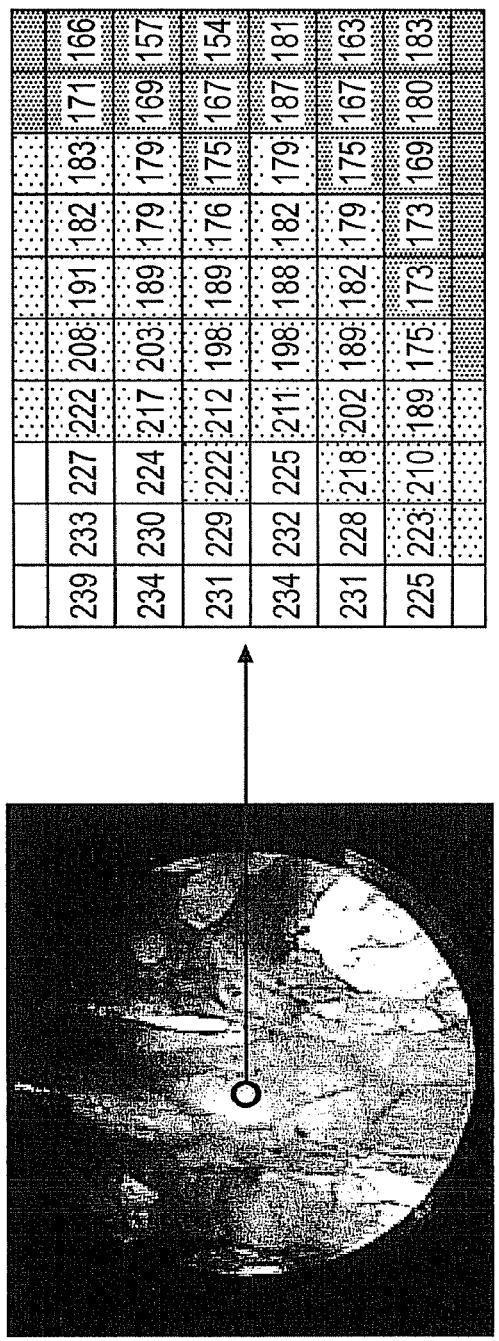
FIG. 6A shows an image obtained from a different sample using apparatus according to an embodiment of the disclosure.
FIG. 6B shows pixel values corresponding to an area of the image.

FIG. 6 (a) shows an image obtained by the same apparatus of a portion of a porous food sample. It can be seen from FIG. 6(b) that the values of amplitude of the signals generated by the detector elements are generally higher than those generated in the case of the more dense sample of FIG. 5. This is because in the case of a more porous sample, a smaller volume of food material constitutes the food sample thereby reducing a volume of food with which the radiation signal can interact, for a given thickness of sample.

Figure 7:
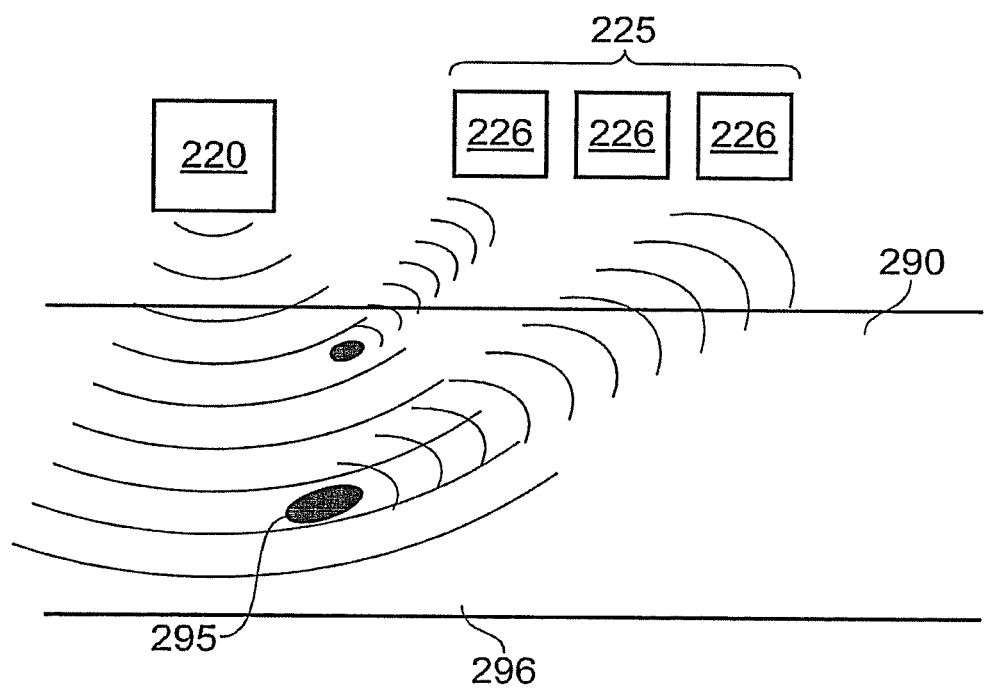
FIG. 7 is a schematic illustration of a reflection mode of operation of apparatus according to the second embodiment.

Embodiments operating in a reflection mode or a variation of the reflection mode such as that described hereinbefore may be configured according to the arrangement shown schematically in FIG. 7. In the embodiment of FIG. 7, it can be seen that the reflective path length of a beam generated by the source 220 is employed to determine the position of particles 295 embedded in a matrix 296 of a sample 290 under inspection.

The apparatus of FIG. 7 is configured to determine a path length of the reflected beam using a detector 225 having an array of detector elements 226 spatially separated with respect to one another.

An apparatus according to at least some of the embodiments preferably does not use a time-resolved technique in order to determine spatial position of the particles. Rather, these embodiments can be configured to determine an amplitude variation of the source signal passed through a portion of a sample. The amplitude of the source signal decreases as the path length of the signal through the article increases.

However, time-resolved techniques may also be used in some of the embodiments and are also considered within the scope of the disclosure.

An apparatus according to at least some of the embodiments may be used to inspect a wide range of materials samples including organic and inorganic materials such as glass, plastic, wood, living and dead tissue, living and dead organisms, and biological materials.

Applications include, without limitation, detection of foreign bodies in articles such as food items. Properties of articles can also be inspected, such as porosity, and density changes variations within a sample may be characterized. Determination of the quality of an article can also be made, for example of food items such as snacks and other items including crisps, cereal bars, biscuits and breads.

Inspection of body parts can also be performed. In some embodiments the apparatus can be configured to measure bone size, and provide images of one or more bones of a body. Inspection of bone fractures is also possible, the quality of images obtained using embodiments that are comparable with x-ray imaging techniques. For example, fractures in areas such as fingers, arms, knees, legs, the chest, heels etc may be inspected.

In a factory environment, packaged goods may be inspected to determine characteristics of a packaged food such as a quantity of food contained in a package, fill height, food quality, and whether or not one or more contaminants of a given type are present.

Non-Limiting Example 1

FIG. 8(a) shows a portion of a sample to be inspected in the form of a sheet of paper having text printed thereon. Two bags made of a plastics material and containing a substance in powder form are overlaid on the paper. FIG. 8(b) shows the sheet of paper folded once, during a process of insertion into an envelope. FIG. 8(c) shows the envelope after sealing.

FIG. 8(d) is an image of the sample of FIG. 8(c) obtained using apparatus according to the first embodiment. Despite the fact that the paper is sealed inside an envelope opaque to visible light, the lettering on the paper is clearly visible and readable in the image.

In an apparatus according to at least some of the embodiments of the disclosure, the image produced is subsequently processed using further image processing technology such as optical character recognition (OCR) in order to enter the text into a database.

The described embodiments can find a wide range of applications relating to security of persons and property. For example, at least some of the described embodiments may be utilized in mailrooms where scanning of mail passing through the mailroom may be performed. Scanning of the mail may involve searching for keywords associated with activities of concern to an organization, such as the words 'bomb' or 'anthrax' etc.

An apparatus according to at least some embodiments may be associated with existing systems configured to scan mail for address and sort code information.

An apparatus according to at least some embodiments may be used to identify the presence of chemical substances such as illegal drugs and other prohibited articles such as firearms, in packages such as envelopes, handbags or suitcases, or being carried on or in the human or animal body.

Non-Limiting Example 2

Figure 9:
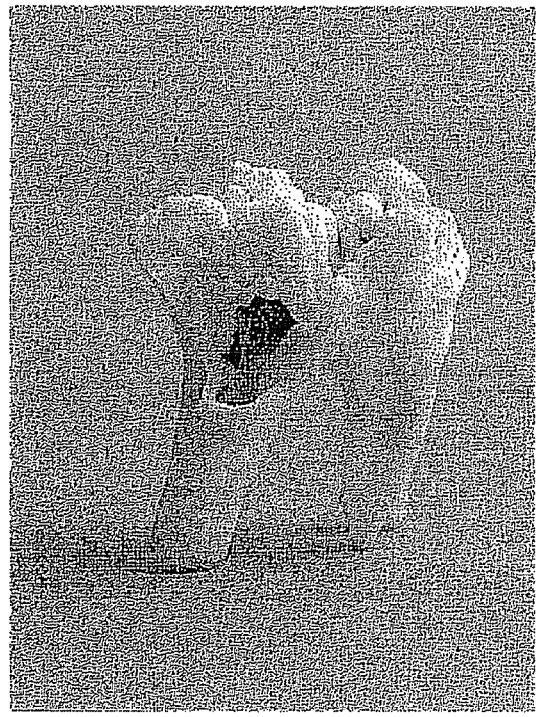
FIG. 9 consists of FIG. 9A, FIG. 9B, FIG. 9C and FIG. 9D which show a series of images corresponding to a second example.

FIG. 9(a) shows a tooth prior to imaging using apparatus according to the first embodiment. FIG. 9(b) shows a lock-in near infrared (NIR) image of the same specimen taken from the same direction of view as the photograph of FIG. 9(a). FIG. 9(c) shows a corresponding contour plot generated from the data of FIG. 9(b).

A region A of relatively high contrast to the surrounding portions of the tooth is apparent in the NIR images. This area corresponds to a relatively low difference between the amplitudes of the reference signal and detector signal. This indicates that the area A corresponds to a region of relatively low density. It can also be seen that a boundary B between enamel and dentine of the tooth appears relatively dark also. The boundary region is also known to be a region of relatively low density.

FIG. 9(d) is a photograph showing a cut-away portion of the tooth of FIG. 9(a). It can be seen that a cavity exists in the tooth. The position of the cavity corresponds to the position of the region of relatively low density of the tooth as revealed in FIGS. 9(b) and (c).

Non-Limiting Example 3

FIG. 10(a) is a photograph of four articles (pen lid A, cotton swab on a wooden stick B, paper clip C and watch battery D) made of a range of materials including either metal, plastics, cotton and wood. The articles are shown prior to packaging inside a cardboard box shown in FIG. 10(b).

FIG. 10(c) is a NIR image of the articles using apparatus according to the first embodiment. FIG. 10(d) shows the image of FIG. 10(c) with reverse contrast. The articles are clearly visible in the images of FIG. 10(c), (d).

It can be seen that NIR imaging is capable of imaging materials that are normally radiolucent to x-rays (such as plastics, wood and cotton) in addition to metals.

The image of FIG. 10(c) was obtained using a NIR source generating near infrared radiation of less than 1 mW of power.

Non-Limiting Example 4

Figure 11A:
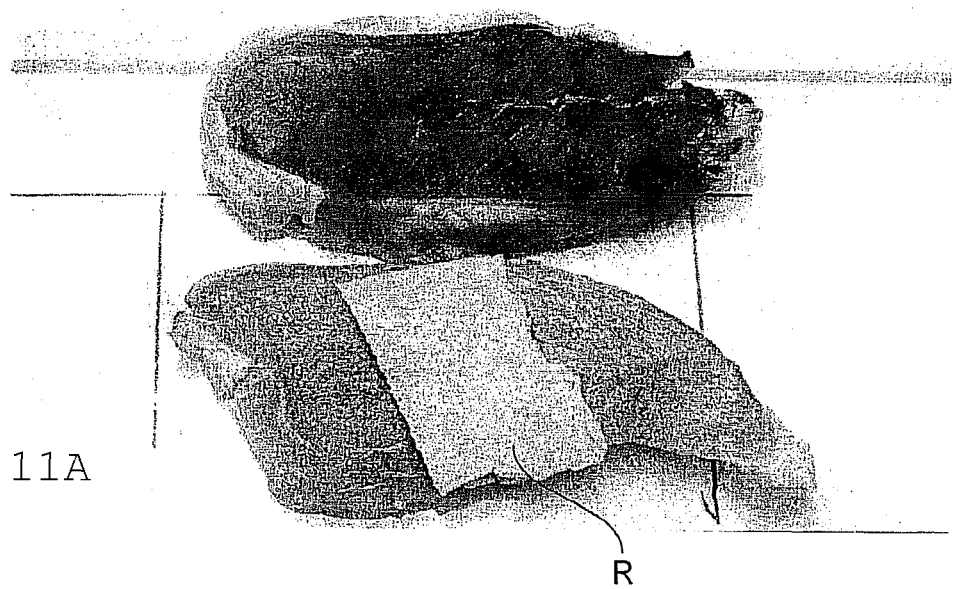
FIG. 11A, FIG. 11B and FIG. 11C show a series of images corresponding to a fourth example.
Figure 11B:
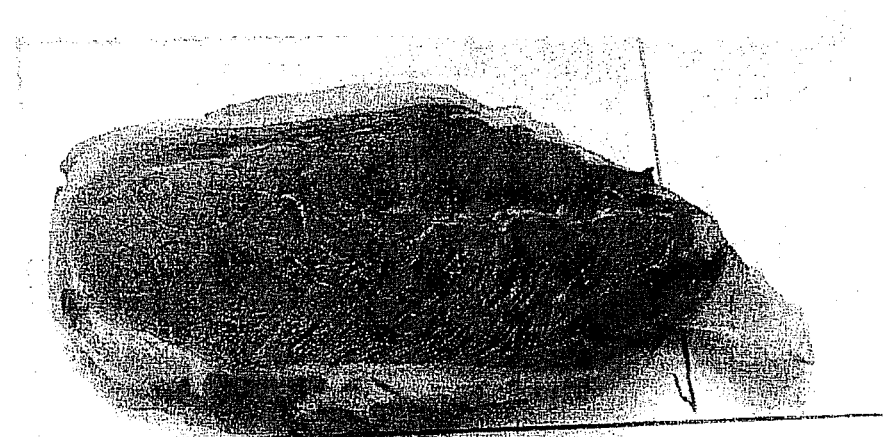
Figure 11C:
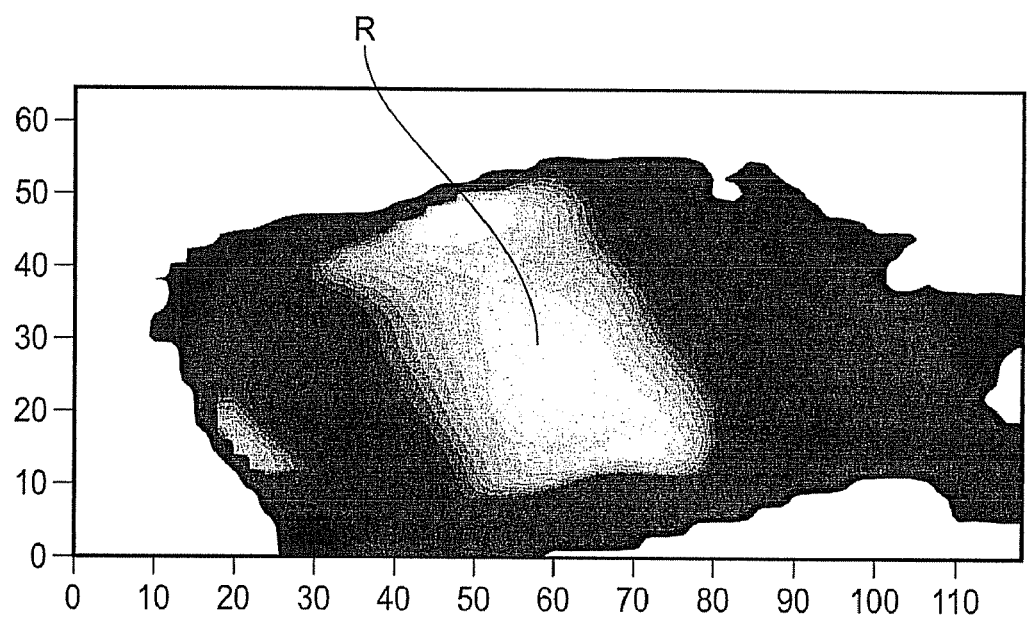

FIG. 11 (a) is a photograph showing two pieces of lean meat (pork) with a section of pork rind R overlaid on one of the pieces (the lower piece) shown in the photograph. FIG. 11 (b) is a photograph taken with the upper piece of pork overlying the lower piece. The pork rind is thereby 'sandwiched' between the two pieces of meat.

FIG. 11 (c) is a lock-in NIR image of the structure shown in FIG. 11 (b). The presence of the pork rind can be clearly seen in the image. The region in which the rind is located is revealed as a region of relatively large difference in amplitude between the reference signal and the detector signal. The pork rind, being of a relatively high fat content, contains a larger proportion of water which attenuates the NIR signal to a greater extent than portions of the sample having a relatively low fat content.

Also apparent in the image are variations in the structure of the pork rind itself. Furthermore, portions of the pork sample that are thinner than other portions also show a variation in contrast compared with the remainder of the pork sample, such as region 'P' of FIG. 11 (c).

Non-Limiting Example 5

Figure 12A:
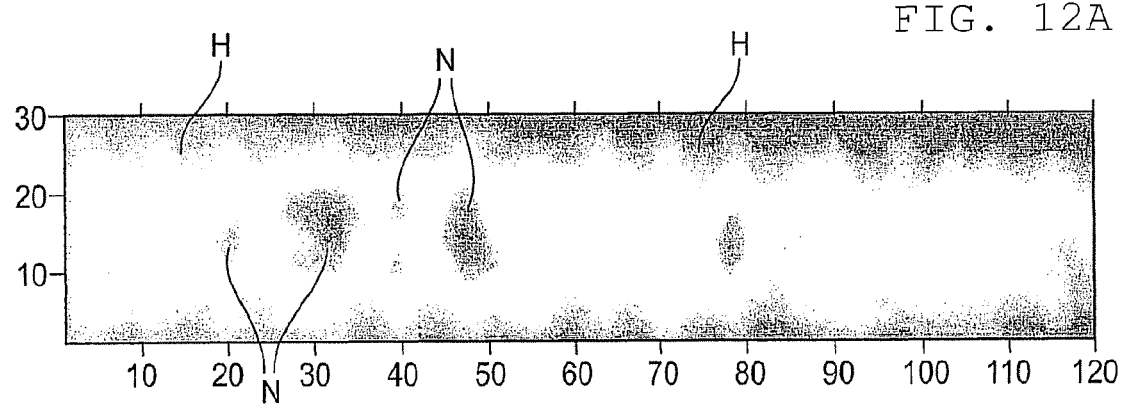
FIG. 12A and FIG. 12B show a series of images corresponding to a fifth example.

FIG. 12(a) shows a NIR image of a chocolate bar made by the Hershey™ Company. The bar has a thickness variation corresponding to the word "HERSHEY'S". The bar also contains almond nuts embedded within the bar.

An apparatus according to the first embodiment is sufficiently sensitive to distinguish the thickness variations of the bar corresponding to the word "HERSHEY'S". The letters show up as dark lettering on a bright background in the image. The letters "H" are labelled in FIG. 12(a) as a guide to the eye.

The almond nuts embedded in the bars are also clearly visible in the image. The nuts are labelled "N" in FIG. 12(a).

Figure 12B:
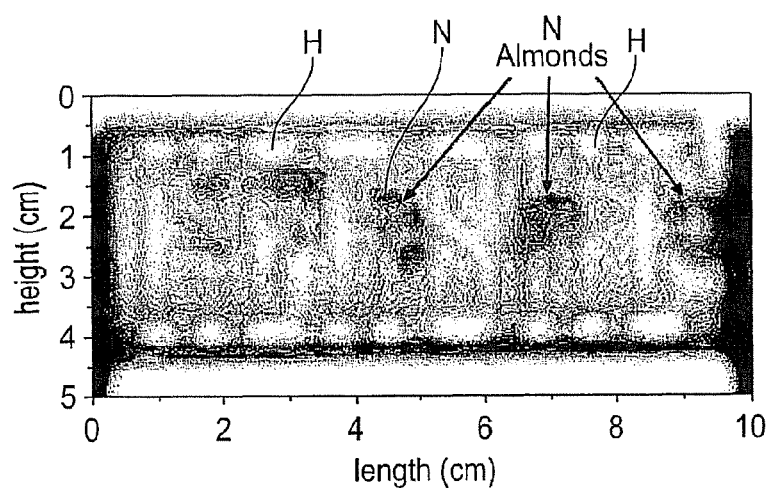

By way of comparison, FIG. 12(b) shows an image of a similar Hershey chocolate bar obtained using a THz imaging system. The system includes a femtosecond pulsed laser Terahertz source and supercooled detector.

The presence of almonds within the chocolate bar, together with the letters "HERSHE" are discernible in the image of FIG. 12(b). The letters "H" are labelled in FIG. 12(b) as a guide to the eye, and nuts are labelled "N".

It is noted that an apparatus according to the first embodiment can be approximately three orders of magnitude lower in cost than the THz imaging system used to obtain the image of FIG. 12(b). Furthermore, an apparatus according to the first embodiment is several hundred times smaller and substantially less costly to maintain.

In some embodiments optical elements such as lenses are not required. This results in reducing a cost of constructing a system according to some of the embodiments.

In an apparatus according to some embodiments, the source can be arranged to emit NIR radiation of a plurality of wavelengths. The source is similarly arranged to detect NIR radiation of a plurality of wavelengths and to measure an intensity of radiation of a given wavelength or range of wavelengths.

An apparatus according to some embodiments can be provided with electronically configurable filter elements. The electronically configurable filter elements can be arranged to allow a user to control a wavelength of radiation permitted to pass into the detectors of the apparatus.

In some embodiments a source configured to emit a range of wavelengths of NIR radiation can be employed.

In at least some embodiments the system can be configured to record the amplitude of a signal detected by the detector as a function of wavelength by varying the wavelength of radiation passed by one or more filter elements associated with the detector. In some embodiments one or more filter elements are associated with the source instead of or in addition to the detector.

In some embodiments a plurality of detectors having different respective filters are provided, to enable simultaneous or near-simultaneous detection of different wavelengths of NIR radiation. In such embodiments, a source configured to emit radiation of a plurality of wavelengths or a range of wavelengths is used. Such embodiments have the advantage of enabling more rapid imaging of an article. Rapid imaging of an article can be particularly important when analysing articles travelling at speed along a conveyor belt, or when imaging living objects.

In some embodiments the source can be configured to scan a beam over a portion of a sample. The beam may be in the form of a point, a line, or a broad area beam. A line source may be generated by means of a cylindrical lens and the line scanned over a portion of a sample.

At least some of the embodiments may be used at modulation frequencies considerably lower than those used in time of flight analysis systems.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the disclosure are to be understood to be applicable to any other aspect, embodiment or example described herein unless incompatible therewith.

All locations, sizes, shapes, measurements, ranges, amounts, angles, voltages, frequencies, component or part locations, configurations, temperatures, weights, dimensions, values, percentages, materials, orientations, applications, uses, etc. discussed above or shown in the drawings are merely by way of example and are not considered limiting and other locations, sizes, shapes, measurements, ranges, amounts, angles, voltages, frequencies, component or part locations, configurations, temperatures, weights, dimensions, values, percentages, materials, orientations, applications, uses, etc. can be chosen and used and all are considered within the scope of the disclosure.

Dimensions of certain parts as shown in the drawings, if any, may have been modified and/or exaggerated for the purpose of clarity of illustration and are not considered limiting.

Unless feature(s), part(s), component(s), characteristic(s) or function(s) described in the specification or shown in the drawings for a claim element, claim step or claim term specifically appear in the claim with the claim element, claim step or claim term, then the inventor does not considered such feature(s), part(s), component(s), characteristic(s) or function(s) to be included for the claim element, claim step or claim term in the claim for examination purposes and when and if the claim element, claim step or claim term is interpreted or construed. Similarly, with respect to any "means for" elements in the claims, the inventor considers such language to require only the minimal amount of features, components, steps, or parts from the specification to achieve the function of the "means for" language and not all of the features, components, steps or parts describe in the specification that are related to the function of the "means for" language.

In the above description, numerous specific details are set forth in order to provide a thorough understanding of the present arrangements and teachings. It will be apparent, however, to one skilled in the art that the present arrangements and teachings may be practiced without limitation to some or all of these specific details.

Although illustrative embodiments of the present teachings and arrangements have been shown and described, other modifications, changes, and substitutions are intended. Accordingly, it is appropriate that the appended claims be construed broadly and in a manner consistent with the scope of the disclosure, as set forth in the following claims.

While the disclosure has been described in certain terms and has disclosed certain embodiments or modifications, persons skilled in the art who have acquainted themselves with the disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

While the foregoing written description of the embodiments enables one of ordinary skill to make and use what is considered presently to be the best mode thereof, those of ordinary skill will understand and appreciate the existence of variations, combinations, and equivalents of the specific embodiments, method, and examples herein. The disclosure therefore not be limited by the above described embodiments, method, and examples. Any feature or combination of features described herein is included within the scope of the disclosure provided that the features of any such combination are not mutually inconsistent.

What is claimed is:

1. Apparatus for imaging an object concealed in an article comprising:
    a controller configured to generate a drive signal having a periodic amplitude variation;
    a source, the source being operable by the controller to emit a source beam thereby to irradiate an article, the source beam comprising a beam of non-ionising electromagnetic radiation having a periodic amplitude variation corresponding to that of the drive signal; and
    a detector, the detector being configured to detect a portion of the source beam that has been transmitted through at least a portion of the article, and to generate a detector signal having an amplitude variation corresponding to the periodic amplitude variation of said portion of the source beam,
    the controller being further configured to perform an auto-correlation or other lock-in detector function between a reference signal related to the drive signal and the detector signal to generate a value corresponding to an amplitude of the portion of the source beam that has been transmitted through at least the portion of the article to image the object concealed in the article in the path of the source beam solely from the amplitudes of the detector signals;
    wherein the detector comprises a photodetector element or an array of photodetector elements.

2. Apparatus as claimed in claim 1 wherein the reference signal is a periodic signal having the same frequency as the drive signal.

3. Apparatus as claimed in claim 1 configured to implement a homodyning function between the reference signal and the detector signal thereby to generate the difference value.

4. Apparatus as claimed in claim 1 wherein the reference signal corresponds to the drive signal.

5. Apparatus as claimed in claim 1 wherein the reference signal is a periodic reference signal having a frequency different from the drive signal.

6. Apparatus as claimed in claim 5 configured to implement a heterodyning function between the reference signal and the detector signal thereby to generate the difference value.

7. Apparatus as claimed in claim 1 wherein the beam of electromagnetic radiation corresponds to electromagnetic radiation having a wavelength in the range 700 to 2000 nm.

8. Apparatus as claimed in claim 1 wherein the periodic amplitude variation of the drive signal and the reference signal corresponds to a square wave signal.

9. Apparatus as claimed in claim 1 wherein the periodic amplitude variation of the drive signal and the periodic amplitude variation of the reference signal correspond to a sine wave signal.

10. Apparatus for imaging an object concealed in an article comprising:
    a controller configured to generate a drive signal having a periodic amplitude variation;
    a source, the source being operable by the controller to emit a source beam thereby to irradiate an article, the source beam comprising a beam of non-ionising electromagnetic radiation having a periodic amplitude variation corresponding to that of the drive signal; and
    a detector, the detector being configured to detect a portion of the source beam that has been transmitted through at least a portion of the article, and to generate a detector signal having an amplitude variation corresponding to the periodic amplitude variation of said portion of the source beam,
    the controller being further configured to perform an auto-correlation or other lock-in detector function between a reference signal related to the drive signal and the detector signal to generate a value corresponding to an amplitude of the portion of the source beam that has been transmitted through at least the portion of the article to image the object concealed in the article in the path of the source beam solely from the amplitudes of the detector signals;
    operable to move the detector with respect to the article to be inspected or operable to move the article to be inspected with respect to the detector.

11. Apparatus as claimed in claim 1 wherein the array is a linear array or a planar array.

12. Apparatus as claimed in claim 1 configured to operate in a transmission mode whereby the detector is arranged to detect a beam of electromagnetic radiation transmitted through the article to be inspected, the detector being provided on a side of the article substantially opposite a side wherein the source is provided.

13. Apparatus as claimed in claim 1 configured to operate in a reflection mode whereby the detector is arranged to detect a beam of electromagnetic radiation reflected by the article to be inspected, the detector being provided on substantially the same side of the article as the source.

14. Apparatus as claimed in claim 1 configurable to operate in either a reflection mode or a transmission mode.

15. Apparatus as claimed in claim 1 wherein the source is configured to emit electromagnetic radiation of a plurality of wavelengths or ranges of wavelength.

16. Apparatus as claimed in claim 1 wherein the detector is configured to detect electromagnetic radiation of a plurality of wavelengths or ranges of wavelength.

17. Apparatus as claimed in claim 16 wherein the detector comprises a tunable filter.

18. Apparatus for imaging an object concealed in an article comprising:
- a controller configured to generate a drive signal having a periodic amplitude variation;
- a source, the source being operable by the controller to emit a source beam thereby to irradiate an article, the source beam comprising a beam of non-ionising electromagnetic radiation having a periodic amplitude variation corresponding to that of the drive signal; and
- a detector, the detector being configured to detect a portion of the source beam that has been transmitted through at least a portion of the article, and to generate a detector signal having an amplitude variation corresponding to the periodic amplitude variation of said portion of the source beam,
- the controller being further configured to perform an autocorrelation or other lock-in detector function between a reference signal related to the drive signal and the detector signal to generate a value corresponding to an amplitude of the portion of the source beam that has been transmitted through at least the portion of the article to image the object concealed in the article in the path of the source beam solely from the amplitudes of the detector signals;
- wherein the detector is configured to detect electromagnetic radiation of a plurality of wavelengths or ranges of wavelength;
- wherein the detector comprises a tunable filter;
- a plurality of detectors, each of said plurality of detectors being configured to detect a respective different wavelength.

19. Apparatus as claimed in claim 16 wherein at least one of said wavelengths corresponds to a characteristic absorption wavelength of a sample.

20. Apparatus as claimed in claim 1 wherein at least one of the source and the detector comprise a fiber optic cable.

21. Apparatus as claimed in claim 20 wherein the source is provided with a fiber optic cable, the cable being arranged to direct the beam of electromagnetic radiation onto the article to be inspected.

22. Apparatus for imaging an object concealed in an article comprising:
- a controller configured to generate a drive signal having a periodic amplitude variation;
- a source, the source being operable by the controller to emit a source beam thereby to irradiate an article, the source beam comprising a beam of non-ionising electromagnetic radiation having a periodic amplitude variation corresponding to that of the drive signal; and
- a detector, the detector being configured to detect a portion of the source beam that has been transmitted through at least a portion of the article, and to generate a detector signal having an amplitude variation corresponding to the periodic amplitude variation of said portion of the source beam,
- the controller being further configured to perform an autocorrelation or other lock-in detector function between a reference signal related to the drive signal and the detector signal to generate a value corresponding to an amplitude of the portion of the source beam that has been transmitted through at least the portion of the article to image the object concealed in the article in the path of the source beam solely from the amplitudes of the detector signals;
- wherein at least one of the source and the detector comprise a fiber optic cable;
- wherein the source is provided with a fiber optic cable, the cable being arranged to direct the beam of electromagnetic radiation onto the article to be inspected;
- wherein the detector is provided with a fiber optic cable arranged to direct electromagnetic radiation from the article onto the detector.

23. Apparatus as claimed in claim 1 wherein the amplitude of the reference signal corresponds to the amplitude of the drive signal.

24. A method of imaging an object concealed in an article comprising:
- generating a drive signal having a periodic amplitude variation;
- generating a source beam of non-ionising electromagnetic radiation having a periodic amplitude variation corresponding to that of the drive signal;
- passing a portion of the source beam through at least a portion of an article to be inspected and to a detector;
- the detector generating a detector signal having an amplitude variation corresponding to the amplitude variation of the portion of the source beam passed to the detector; and
- performing an autocorrelation or other lock-in detector function between a reference signal related to the drive signal and the detector signal to generate a value corresponding to an amplitude of the portion of the source beam that has been transmitted through the at least the portion of the article to image the object therein in the path of the source beam solely from the amplitudes of the detector signals;
- generating a difference value corresponding to a difference between the amplitude of the detector signal and the amplitude of a reference signal.

25. A method as claimed in claim 24 whereby the source beam corresponds to electromagnetic radiation having a wavelength in the range 700 to 2000 nm.

26. The method as claimed in claim 24 further comprising detecting, by the detector, a beam of electromagnetic radiation transmitted through the article to be inspected, the detector being provided on a side of the article substantially opposite a side of a source of the source beam.

27. The method as claimed in claim 24 further comprising detecting, by the detector, a beam of electromagnetic radiation reflected by the article to be inspected, the detector being provided on substantially a same side of the article as a source of the source beam.

28. Apparatus for imaging an object concealed in an article comprising:
- a controller configured to generate a drive signal having a periodic amplitude variation;
- a source, the source being operable by the controller to emit a source beam thereby to irradiate an article, the source beam comprising a beam of non-ionising electromagnetic radiation having a periodic amplitude variation corresponding to the drive signal; and
- a detector, the detector being configured to detect a portion of the source beam that has been transmitted through at least a portion of the article, and to generate a detector signal having an amplitude variation corresponding to the periodic amplitude variation of said portion of the source beam;

the controller being further configured to perform an autocorrelation or other lock-in detector function between a reference signal related to the drive signal and the detector signal to generate a value corresponding to an amplitude of the portion of the source beam that has been transmitted through at least the portion of the article to image the object concealed in the article in the path of the soIMIMrce beam solely from the amplitudes of the detector signals, wherein the reference signal is a periodic signal having the same frequency as the drive signal and corresponds to the drive signal, the apparatus being configured to implement a homodyning function between the reference signal and the detector signal thereby to generate the difference value;

wherein the detector comprises a photodetector element or an array of photodetector elements.

29. A method of imaging an object concealed in an article comprising:

generating a drive signal having a periodic amplitude variation;

generating a source beam of non-ionising electromagnetic radiation having a periodic amplitude variation corresponding to the drive signal;

passing a portion of the source beam through at least a portion of the article to be inspected and to a detector;

the detector generating a detector signal having an amplitude variation corresponding to the amplitude variation of the portion of the source beam passed to the detector; and performing an autocorrelation or other lock-in detector function between a reference signal related to the drive signal and the detector signal to generate a value corresponding to an amplitude of the portion of the source beam that has been transmitted through the at least the portion of the article to image the object therein in the path of the source beam solely from the amplitudes of the detector signals by implementing a homodyning function between the reference signal and the detector signal;

wherein the detector comprises a photodetector element or an array of photodetector elements.

* * * * *